United States Patent
Natanzon et al.

(10) Patent No.: US 8,645,458 B2
(45) Date of Patent: Feb. 4, 2014

(54) SYSTEMS AND METHODS FOR DELIVERING MEDIA CONTENT AND IMPROVING DIAGNOSTIC READING EFFICIENCY

(75) Inventors: Alexander Natanzon, Upper Saddle River, NJ (US); Dmitry Pavlov, New Paltz, NY (US); Alexander Jurovitsky, Mahwah, NJ (US); Andrei Leontiev, South Burlington, VT (US); Michael Plavnik, Mahwah, NJ (US); Vitaly Roginsky, Mahwah, NJ (US); Alexander Vitchevsky, Haifa, IL (US)

(73) Assignee: General Electric Company, Schenectady, NY (US)

( * ) Notice: Subject to any disclaimer, the term of this patent is extended or adjusted under 35 U.S.C. 154(b) by 493 days.

(21) Appl. No.: 12/275,064

(22) Filed: Nov. 20, 2008

(65) Prior Publication Data

US 2009/0132636 A1   May 21, 2009

Related U.S. Application Data

(60) Provisional application No. 60/989,378, filed on Nov. 20, 2007, provisional application No. 61/015,550, filed on Dec. 20, 2007, provisional application No. 60/989,375, filed on Nov. 20, 2007.

(51) Int. Cl.
*G06F 15/16* (2006.01)
(52) U.S. Cl.
USPC ............... 709/203; 709/217; 709/223; 705/2; 382/232
(58) Field of Classification Search
USPC ......... 709/203, 223, 224, 225, 231, 232, 233, 709/235, 238, 239, 240, 217; 705/2; 382/232
See application file for complete search history.

(56) References Cited

U.S. PATENT DOCUMENTS

| | | | |
|---|---|---|---|
| 6,424,996 B1 * | 7/2002 | Killcommons et al. | 709/206 |
| 7,038,588 B2 * | 5/2006 | Boone et al. | 340/573.1 |
| 7,093,028 B1 * | 8/2006 | Shao et al. | 709/240 |
| 7,382,729 B2 * | 6/2008 | Honda et al. | 370/235 |
| 7,929,793 B2 * | 4/2011 | Gering et al. | 382/239 |
| 2002/0016721 A1 * | 2/2002 | Mason et al. | 705/3 |
| 2002/0083075 A1 * | 6/2002 | Brummel et al. | 707/102 |
| 2003/0050801 A1 * | 3/2003 | Ries et al. | 705/2 |
| 2005/0182846 A1 * | 8/2005 | Schofield et al. | 709/232 |
| 2006/0031095 A1 * | 2/2006 | Barth et al. | 705/2 |
| 2006/0095429 A1 * | 5/2006 | Abhyankar et al. | 707/7 |
| 2007/0269117 A1 * | 11/2007 | Ernvik et al. | 382/232 |
| 2008/0294454 A1 * | 11/2008 | Taha | 705/2 |
| 2009/0150184 A1 * | 6/2009 | Spahn | 705/3 |
| 2010/0153132 A1 * | 6/2010 | Barth et al. | 705/2 |

* cited by examiner

*Primary Examiner* — Lashonda Jacobs
(74) *Attorney, Agent, or Firm* — Hanley, Flight and Zimmerman, LLC

(57) ABSTRACT

Certain embodiments provide systems and methods for image delivery in a picture archiving and communication system. Certain embodiments provide a method for transferring image data via a delivery chain for display at a client workstation. The method includes creating a data list describing image data to be delivered to implement an imaging workflow. The method includes establishing a general loading plan to specify a recommended priority for delivery of the image data in the data list. The method includes generating a node loading plan for each node in the delivery chain based on the general loading plan. The method includes reconciling at least one of the general loading plan and the node loading plan. The method includes delivering the image data via the nodes of the delivery chain based on the general loading plan, the node loading plan for each node in the delivery chain, and the data list.

22 Claims, 5 Drawing Sheets

SYSTEMS AND METHODS FOR DELIVERING MEDIA CONTENT AND IMPROVING DIAGNOSTIC READING EFFICIENCY

RELATED APPLICATIONS

The present application claims the benefit of priority to U.S. Provisional Application No. 60/989,378, filed on Nov. 20, 2007, entitled "Special Methodic for Delivering Media Content", U.S. Provisional Application No. 61/015,550, filed on Dec. 20, 2007, entitled "Improvement of Diagnostic Reading Efficiency Through Reduction of the Latency Time of Opening New Exam", and U.S. Provisional Application No. 60/989,375, filed on Nov. 20, 2007, entitled "Special Methodic for Image Handling and Presentation", each of which is herein incorporated by reference in its entirety.

FEDERALLY SPONSORED RESEARCH OR DEVELOPMENT

[Not Applicable]

MICROFICHE/COPYRIGHT REFERENCE

[Not Applicable]

BACKGROUND OF THE INVENTION

Healthcare environments, such as hospitals or clinics, include information systems, such as hospital information systems (HIS), radiology information systems (RIS), clinical information systems (CIS), and cardiovascular information systems (CVIS), and storage systems, such as picture archiving and communication systems (PACS), library information systems (LIS), and electronic medical records (EMR). Information stored may include patient medical histories, imaging data, test results, diagnosis information, management information, and/or scheduling information, for example. The information may be centrally stored or divided at a plurality of locations. Healthcare practitioners may desire to access patient information or other information at various points in a healthcare workflow. For example, during and/or after surgery, medical personnel may access patient information, such as images of a patient's anatomy, that are stored in a medical information system. Radiologist and/or other clinicians may review stored images and/or other information, for example.

Using a PACS and/or other workstation, a clinician, such as a radiologist, may perform a variety of activities, such as an image reading, to facilitate a clinical workflow. A reading, such as a radiology or cardiology procedure reading, is a process of a healthcare practitioner, such as a radiologist or a cardiologist, viewing digital images of a patient. The practitioner performs a diagnosis based on a content of the diagnostic images and reports on results electronically (e.g., using dictation or otherwise) or on paper. The practitioner, such as a radiologist or cardiologist, typically uses other tools to perform diagnosis. Some examples of other tools are prior and related prior (historical) exams and their results, laboratory exams (such as blood work), allergies, pathology results, medication, alerts, document images, and other tools. For example, a radiologist or cardiologist typically looks into other systems such as laboratory information, electronic medical records, and healthcare information when reading examination results.

PACS were initially used as an information infrastructure supporting storage, distribution, and diagnostic reading of images acquired in the course of medical examinations. As PACS developed and became capable of accommodating vast volumes of information and its secure access, PACS began to expand into the information-oriented business and professional areas of diagnostic and general healthcare enterprises. For various reasons, including but not limited to a natural tendency of having one information technology (IT) department, one server room, and one data archive/backup for all departments in healthcare enterprise, as well as one desktop workstation used for all business day activities of any healthcare professional, PACS is considered as a platform for growing into a general IT solution for the majority of IT oriented services of healthcare enterprises.

Medical imaging devices now produce diagnostic images in a digital representation. The digital representation typically includes a two dimensional raster of the image equipped with a header including collateral information with respect to the image itself, patient demographics, imaging technology, and other data used for proper presentation and diagnostic interpretation of the image. Often, diagnostic images are grouped in series each series representing images that have some commonality and differ in one or more details. For example, images representing anatomical cross-sections of a human body substantially normal to its vertical axis and differing by their position on that axis from top (head) to bottom (feet) are grouped in so-called axial series. A single medical exam, often referred as a "study" or an "exam" typically includes one or more series of images, such as images exposed before and after injection of contrast material or images with different orientation or differing by any other relevant circumstance(s) of imaging procedure. The digital images are forwarded to specialized archives equipped with proper means for safe storage, search, access, and distribution of the images and collateral information for successful diagnostic interpretation.

Diagnostic physicians that read a study digitally via access to a PACS from a local workstation currently suffer from a significant problem associated with the speed of study opening and making studies available for review where the reading performance of some radiologists requires opening up to 30 MRI studies an hour. Currently, a significant portion of a physician's time is spent just opening the study at the local workstation. When a user is reading one study after another, a switch from a study just read to the next study to be read requires two mouse clicks (one to close the current study and one to open the next study via the physician worklist), introduces delay between those clicks necessary for the refresh of the study list, and an additional delay for loading the next study.

Secondly, current mechanisms for loading a study do not allow for negotiation between instances of a diagnostic viewer that are invoked at the same time and share network bandwidth and processing capability on the workstation trying to simultaneously downloading multiple studies and respond to a user interface reading the study. This causes all studies to load more slowly so that it takes proportionally longer for the first study to become ready for reading. Such an approach is especially detrimental for cases when the first study needs to be downloaded as fast as possible, for example, when reading mammography studies.

BRIEF SUMMARY OF THE INVENTION

Certain embodiments of the present invention provide systems and methods for image delivery in a picture archiving and communication system.

Certain embodiments provide a method for transferring image data via a delivery chain for display at a client workstation. The method includes creating a data list describing image data to be delivered to implement an imaging workflow. The method also includes establishing a general loading plan to specify a recommended priority for delivery of the image data in the data list. The method further includes generating a node loading plan for each node in the delivery chain based on the general loading plan. The method additionally includes reconciling at least one of the general loading plan and the node loading plan. The method also includes delivering the image data via the nodes of the delivery chain based on the general loading plan, the node loading plan for each node in the delivery chain, and the data list.

Certain embodiments provide a picture archiving and communication system including a delivery chain including a plurality of nodes retrieving image data from storage and transmitting the image data from a server to a workstation for display. The system also includes a processor and associated memory including a data list and a general loading plan. The data list describes image data to be delivered to implement an imaging workflow, and the general loading plan specifies a recommended priority for delivery of the image data in the data list. The processor provides a node loading plan to each node in the delivery chain based on the general loading plan. The delivery chain operates with the data list, general loading plan, and each node loading plan to deliver requested image data via the delivery chain.

Certain embodiments provide a computer readable medium having a set of instructions for execution on a computing device. The set of instructions execute a method for transferring image data via a delivery chain for display at a client workstation. The method includes creating a data list describing image data to be delivered to implement an imaging workflow. The method also includes establishing a general loading plan to specify a recommended priority for delivery of the image data in the data list. The method further includes generating a node loading plan for each node in the delivery chain based on the general loading plan. The method additionally includes reconciling at least one of the general loading plan and the node loading plan. The method also includes delivering the image data via the nodes of the delivery chain based on the general loading plan, the node loading plan for each node in the delivery chain, and the data list.

Figure 1:
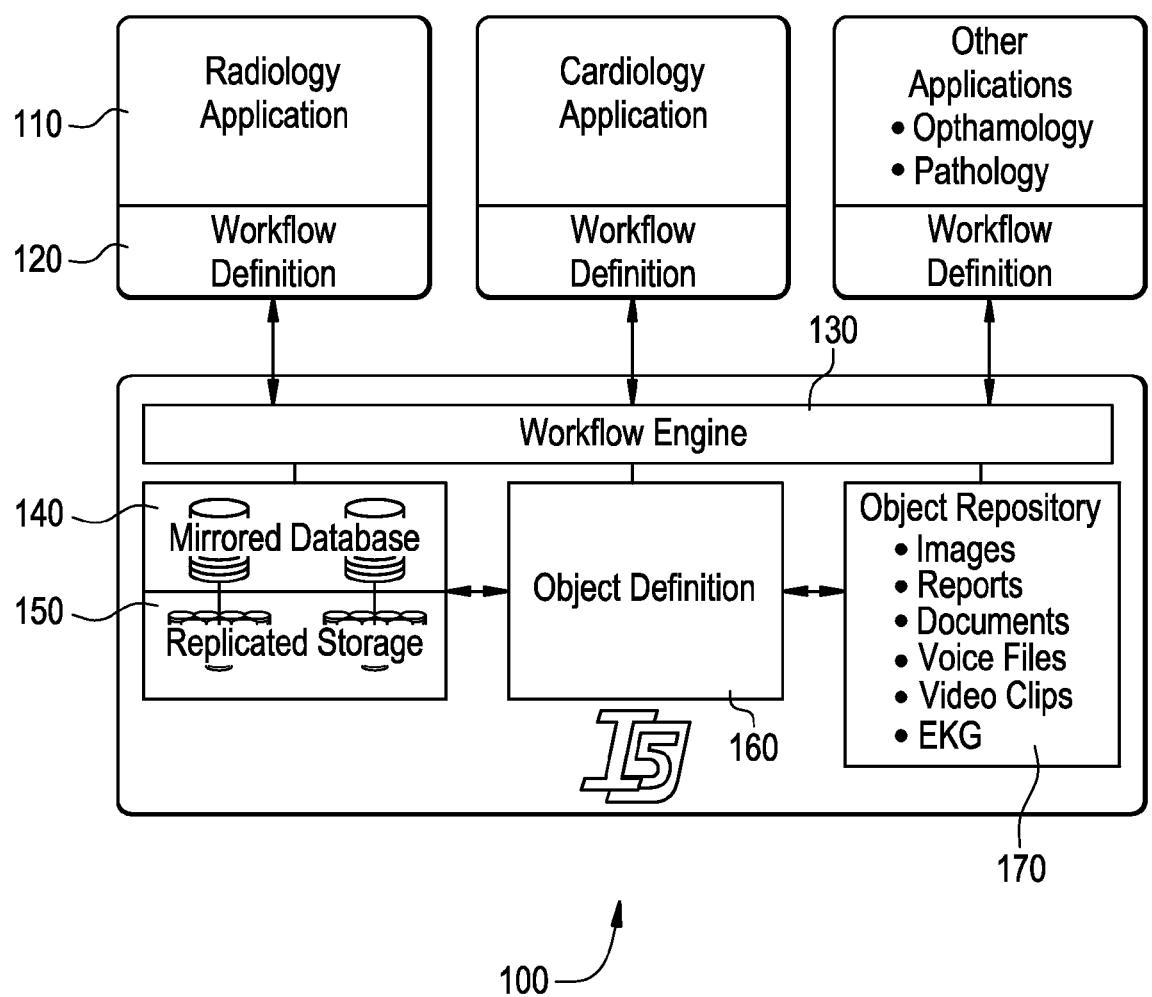
FIG. 1 demonstrates a business and application diagram for PACS information system in accordance with an embodiment of the present invention.

The foregoing summary, as well as the following detailed description of certain embodiments of the present invention, will be better understood when read in conjunction with the appended drawings. For the purpose of illustrating the invention, certain embodiments are shown in the drawings. It should be understood, however, that the present invention is not limited to the arrangements and instrumentality shown in the attached drawings.

DETAILED DESCRIPTION OF THE INVENTION

Certain embodiments relate to reading and interpretation of diagnostic imaging studies, stored in their digital representation and searched, retrieved, and read using a PACS and/or other clinical system. In certain embodiments, images can be stored on a centralized server while reading is performed from one or more remote workstations connected to the server via electronic information links. Remote viewing creates a certain latency between a request for image(s) for diagnostic reading and availability of the images on a local workstation for navigation and reading. Additionally, a single server often provides images for a plurality of workstations that can be connected through electronic links with different bandwidths. Differing bandwidth can create a problem with respect to balanced splitting of the transmitting capacity of the central server between multiple clients. Further, diagnostic images can be stored in one or more advanced compression formats allowing for transmission of a lossy image representation that is continuously improving until finally reaching a lossless, more exact representation. In addition, a number of images produced per standard medical examination continues to grow, reaching 2,500 to 4,000 images per one typical computed tomography (CT) exam compared to 50 images per one exam a decade ago.

Certain embodiments provide "smart" storage, transfer, usability and presentation of diagnostic images to help alleviate certain problems previously found in digital picture archiving and communication systems (PACS) including but not limited to: (1) a load on an information system, (2) a load on a network data transferring system, (3) heavy requirements to image content storage volume; and (4) latency time for image retrieval, image transmission, and image rendering on a diagnostic workstation's display. Additionally, certain embodiments help facilitate improved ergonomic screen layout, image manipulation, and image presentation for a diagnostic physician to provide more effective visual perception and diagnostic reading.

Prior to archiving, digital images are subjected to different types of compression for minimization of required capacity of storage and bandwidth of information links. One compression standard used in medical imaging and other media content information systems is the JPEG2000 standard, which allows decomposition of an image into multiple compression layers, each layer representing a certain scale and resolution of the image. Transmitting a few of the most coarse layers of the image may be used to represent the general image but may compromise the image quality with respect to finer image details. Although coarse image representation is not sufficient for diagnostic visual perception, it still can be suitable for getting a first impression of anatomical scene, navigating through a stack of images to identify a clinically relevant anatomical area, and/or any other interactive preprocessing of the image or whole medical examination. Subsequent transmission and decompression of additional layers enriches the image with fine details and, upon transmission of all layers, reproduce the image in its exact representation.

In certain embodiments, rather than having only one preferred compression scheme (e.g., jpeg, wavelet, layered, etc.), several compression schemes can be provided in a single system, including uncompressed files. Certain embodiments provide a variety of techniques for handling thin slice data.

For example, several thin slices and one thick slice can be combined. Certain embodiments utilize similarity of neighboring images to take advantage of common values to compress images. For example, information common to the slices and information regarding differences between the slices are stored so that the image slices can be compressed using an appropriate mechanism and can be delivered to a workstation on request to enable fine grain reading of diagnostic images. Certain embodiments find applicability for both long term and short term storage depending on a combination of price of storage, price of transfer, load on local and remote networks, price of compression (e.g., time), etc.

Certain embodiments provide systems and methods for transfer, improved storage, and improved presentation and perception of diagnostic images and other viewable media in order to help reduce system cost and complexity as well as physician waiting time and to help improve performance and work quality for a physician (and/or other workstation operator) to implement a workflow associated with reading, reviewing, and/or other utilization of the media.

Certain embodiments provide an information system for a healthcare enterprise including a PACS system for radiology and/or other subspecialty system as demonstrated by the business and application diagram in FIG. 1. The system 100 of FIG. 1 includes a clinical application 110, such as a radiology, cardiology, ophthalmology, pathology, and/or application. The system 100 also includes a workflow definition 120 for each application 110. The workflow definitions 120 communicate with a workflow engine 130. The workflow engine 130 is in communication with a mirrored database 140, object definitions 60, and an object repository 170. The mirrored database 140 is in communication with a replicated storage 150. The object repository 170 includes data such as images, reports, documents, voice files, video clips, EKG information, etc.

Figure 2:
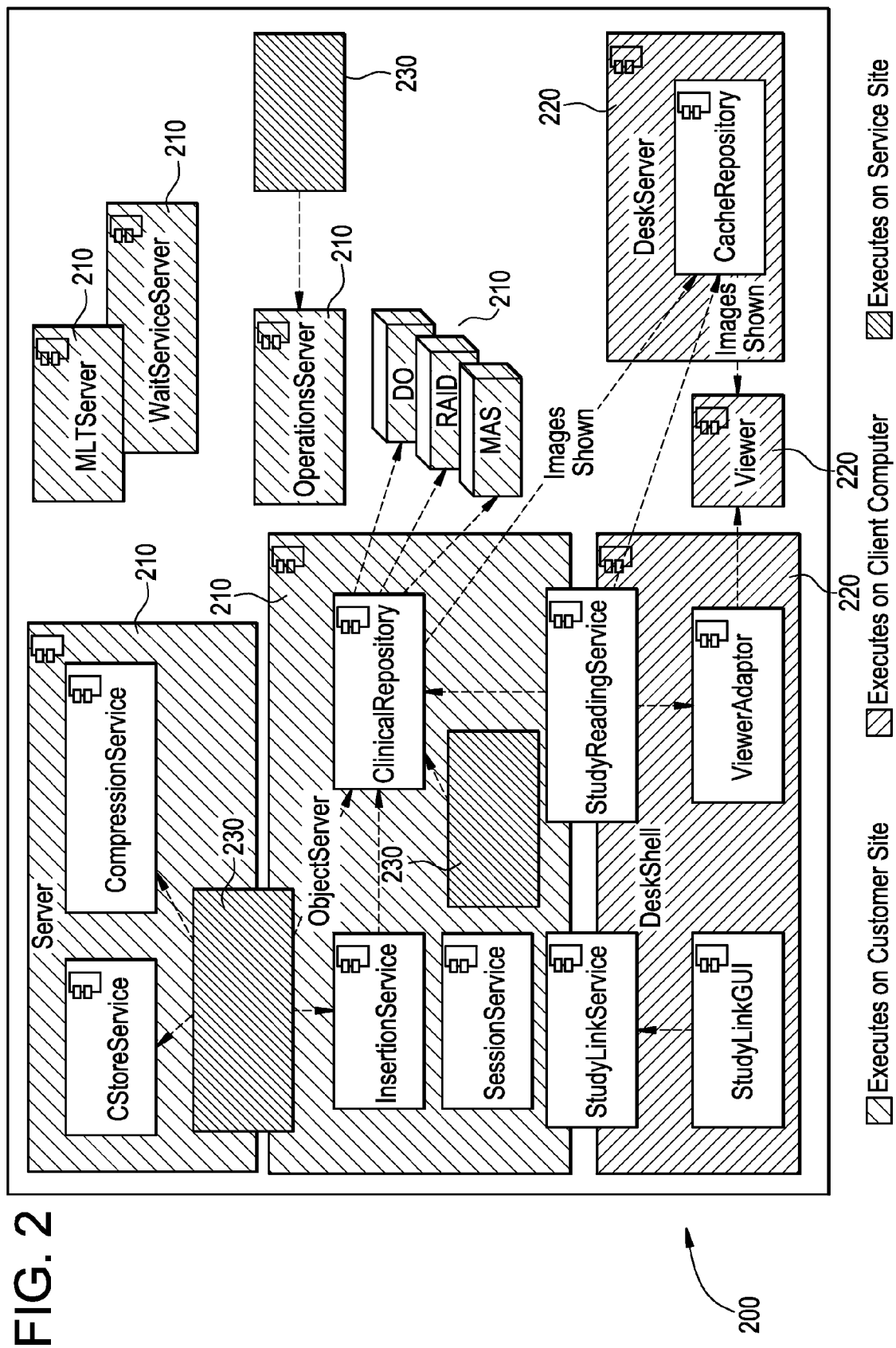
FIG. 2 illustrates an embodiment of an information system delivering application and business content in accordance with an embodiment of the present invention.

An embodiment of an information system that delivers application and business goals is presented in FIG. 2. The specific arrangement and contents of the assemblies constituting this embodiment bears sufficient novelty and constitute part of certain embodiments of the present invention. The information system 200 of FIG. 2 demonstrates services divided among a service site 230, a customer site 210, and a client computer 220. For example, a Dicom Server, HL7 Server, Web Services Server, Operations Server, database and other storage, an Object Server, and a Clinical Repository execute on a customer site 210. A Desk Shell, a Viewer, and a Desk Server execute on a client computer 220. A Dicom Controller, Compiler, and the like execute on a service site 230. Thus, operational and data workflow may be divided, and only a small display workload is placed on the client computer 220, for example.

Certain embodiments provide an architecture and framework for a variety of clinical applications. The framework can include front-end components including but not limited to a Graphical User Interface (GUI) and can be a thin client and/or thick client system to varying degree, which some or all applications and processing running on a client workstation, on a server, and/or running partially on a client workstation and partially on a server, for example.

Figure 3:
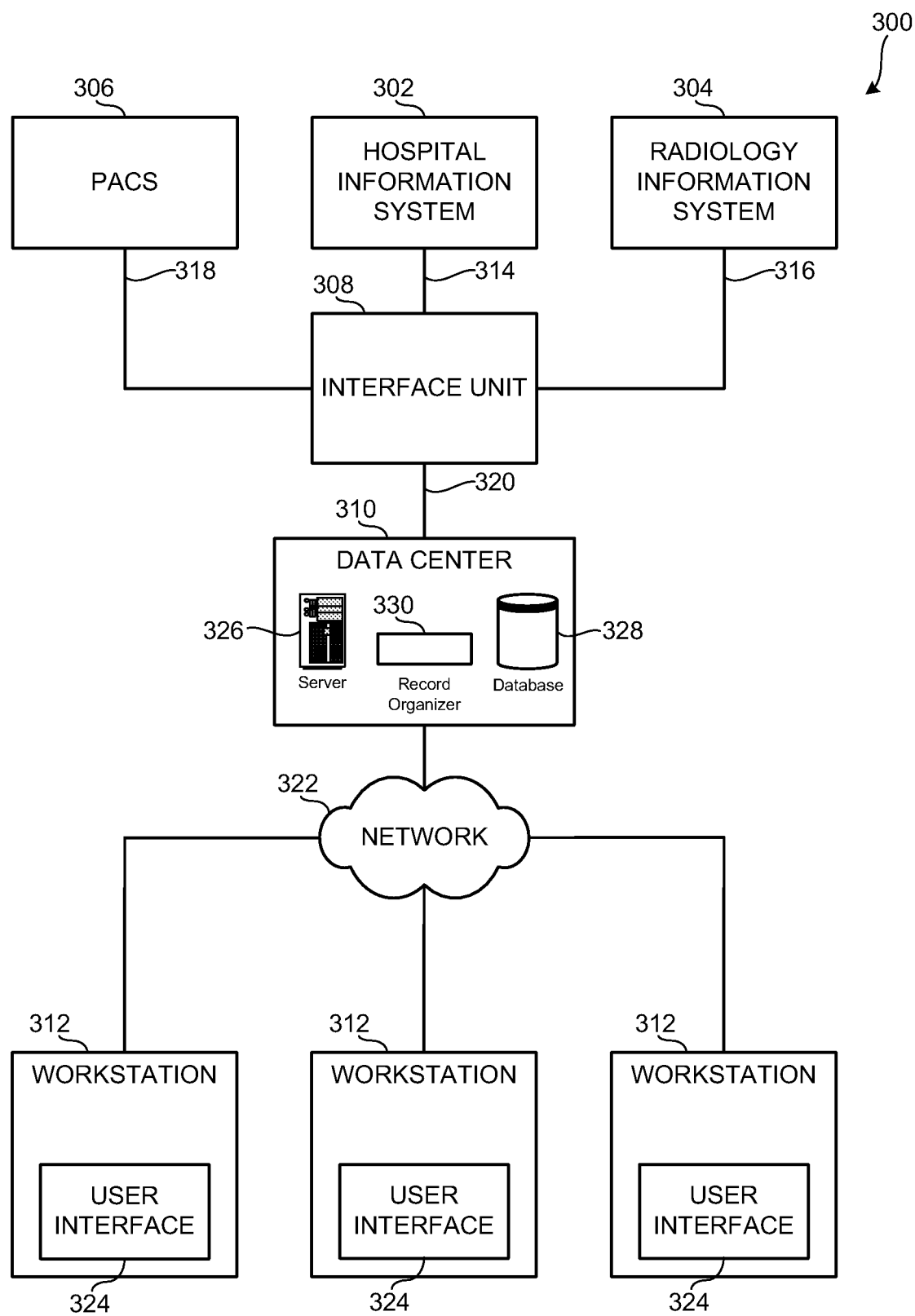
FIG. 3 illustrates a block diagram of an example clinical information system that may be used to implement systems and methods described herein.

FIG. 3 shows a block diagram of an example clinical information system 300 capable of implementing the example methods and systems described herein. The example clinical information system 300 includes a hospital information system ("HIS") 302, a radiology information system ("RIS") 304, a picture archiving and communication system ("PACS") 306, an interface unit 308, a data center 310, and a plurality of workstations 312. In the illustrated example, the HIS 302, the RIS 304, and the PACS 306 are housed in a healthcare facility and locally archived. However, in other implementations, the HIS 302, the RIS 304, and/or the PACS 306 may be housed one or more other suitable locations. In certain implementations, one or more of the PACS 306, RIS 304, HIS 302, etc., can be implemented remotely via a thin client and/or downloadable software solution. Furthermore, one or more components of the clinical information system 300 may be combined and/or implemented together. For example, the RIS 304 and/or the PACS 306 may be integrated with the HIS 302; the PACS 306 may be integrated with the RIS 304; and/or the three example information systems 302, 304, and/or 306 may be integrated together. In other example implementations, the clinical information system 300 includes a subset of the illustrated information systems 302, 304, and/or 306. For example, the clinical information system 300 may include only one or two of the HIS 302, the RIS 304, and/or the PACS 306. Preferably, information (e.g., scheduling, test results, observations, diagnosis, etc.) is entered into the HIS 302, the RIS 304, and/or the PACS 306 by healthcare practitioners (e.g., radiologists, physicians, and/or technicians) before and/or after patient examination.

The HIS 302 stores medical information such as clinical reports, patient information, and/or administrative information received from, for example, personnel at a hospital, clinic, and/or a physician's office. The RIS 304 stores information such as, for example, radiology reports, messages, warnings, alerts, patient scheduling information, patient demographic data, patient tracking information, and/or physician and patient status monitors. Additionally, the RIS 304 enables exam order entry (e.g., ordering an x-ray of a patient) and image and film tracking (e.g., tracking identities of one or more people that have checked out a film). In some examples, information in the RIS 304 is formatted according to the HL-7 (Health Level Seven) clinical communication protocol.

The PACS 306 stores medical images (e.g., x-rays, scans, three-dimensional renderings, etc.) as, for example, digital images in a database or registry. In some examples, the medical images are stored in the PACS 306 using the Digital Imaging and Communications in Medicine ("DICOM") format. Images are stored in the PACS 306 by healthcare practitioners (e.g., imaging technicians, physicians, radiologists) after a medical imaging of a patient and/or are automatically transmitted from medical imaging devices to the PACS 306 for storage. In some examples, the PACS 306 may also include a display device and/or viewing workstation to enable a healthcare practitioner to communicate with the PACS 306.

The interface unit 308 includes a hospital information system interface connection 314, a radiology information system interface connection 316, a PACS interface connection 318, and a data center interface connection 320. The interface unit 308 facilities communication among the HIS 302, the RIS 304, the PACS 306, and/or the data center 310. The interface connections 314, 316, 318, and 320 may be implemented by, for example, a Wide Area Network ("WAN") such as a private network or the Internet. Accordingly, the interface unit 308 includes one or more communication components such as, for example, an Ethernet device, an asynchronous transfer mode ("ATM") device, an 802.11 device, a DSL modem, a cable modem, a cellular modem, etc. In turn, the data center 310 communicates with the plurality of workstations 312, via a network 322, implemented at a plurality of locations (e.g., a hospital, clinic, doctor's office, other medical office, or terminal, etc.). The network 322 is implemented by, for example, the Internet, an intranet, a private network, a wired or wireless Local Area Network, and/or a wired or wireless Wide Area Network. In some examples, the interface unit 308 also includes a broker (e.g., a Mitra Imaging's PACS Broker) to allow medical information and medical images to be transmitted together and stored together.

In operation, the interface unit 308 receives images, medical reports, administrative information, and/or other clinical information from the information systems 302, 304, 306 via the interface connections 314, 316, 318. If necessary (e.g., when different formats of the received information are incompatible), the interface unit 308 translates or reformats (e.g., into Structured Query Language ("SQL") or standard text) the medical information, such as medical reports, to be properly stored at the data center 310. Preferably, the reformatted medical information may be transmitted using a transmission protocol to enable different medical information to share common identification elements, such as a patient name or social security number. Next, the interface unit 308 transmits the medical information to the data center 310 via the data center interface connection 320. Finally, medical information is stored in the data center 310 in, for example, the DICOM format, which enables medical images and corresponding medical information to be transmitted and stored together.

The medical information is later viewable and easily retrievable at one or more of the workstations 312 (e.g., by their common identification element, such as a patient name or record number). The workstations 312 may be any equipment (e.g., a personal computer) capable of executing software that permits electronic data (e.g., medical reports) and/or electronic medical images (e.g., x-rays, ultrasounds, MRI scans, etc.) to be acquired, stored, or transmitted for viewing and operation. The workstations 312 receive commands and/or other input from a user via, for example, a keyboard, mouse, track ball, microphone, etc. As shown in FIG. 3, the workstations 312 are connected to the network 322 and, thus, can communicate with each other, the data center 310, and/or any other device coupled to the network 322. The workstations 312 are capable of implementing a user interface 324 to enable a healthcare practitioner to interact with the clinical information system 300. For example, in response to a request from a physician, the user interface 324 presents a patient medical history. Additionally, the user interface 324 includes one or more options related to the example methods and apparatus described herein to organize such a medical history using classification and severity parameters.

The example data center 310 of FIG. 3 is an archive to store information such as, for example, images, data, medical reports, and/or, more generally, patient medical records. In addition, the data center 310 may also serve as a central conduit to information located at other sources such as, for example, local archives, hospital information systems/radiology information systems (e.g., the HIS 302 and/or the RIS 304), or medical imaging/storage systems (e.g., the PACS 306 and/or connected imaging modalities). That is, the data center 310 may store links or indicators (e.g., identification numbers, patient names, or record numbers) to information. In the illustrated example, the data center 310 is managed by an application server provider ("ASP") and is located in a centralized location that may be accessed by a plurality of systems and facilities (e.g., hospitals, clinics, doctor's offices, other medical offices, and/or terminals). In some examples, the data center 310 may be spatially distant from the HIS 302, the RIS 304, and/or the PACS 306 (e.g., at General Electric® headquarters).

The example data center 310 of FIG. 3 includes a server 326, a database 328, and a record organizer 330. The server 326 receives, processes, and conveys information to and from the components of the clinical information system 300. The database 328 stores the medical information described herein and provides access thereto. The example record organizer 330 of FIG. 3 manages patient medical histories, for example. The record organizer 330 can also assist in procedure scheduling, for example.

Figure 4:
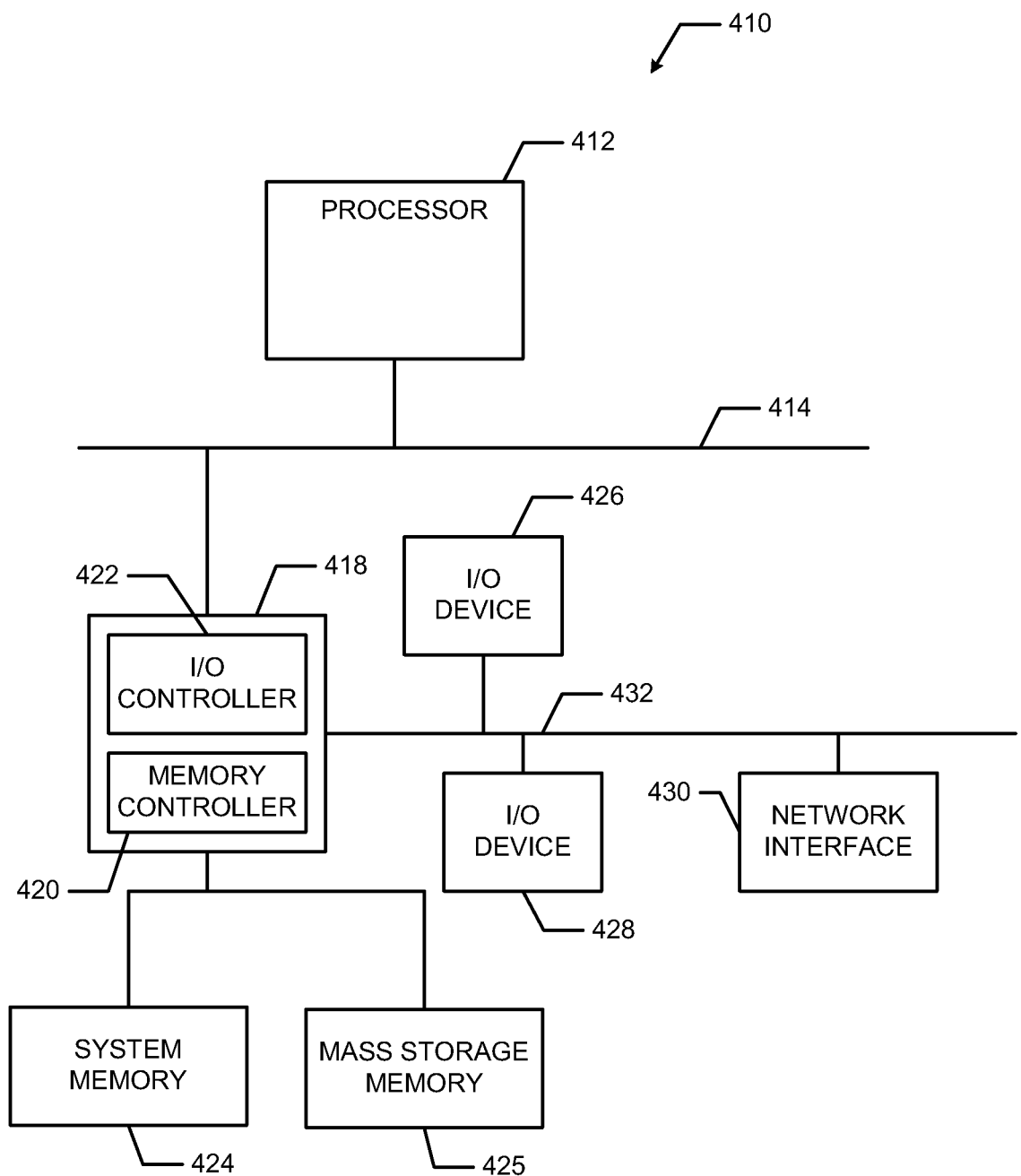
FIG. 4 shows a block diagram of an example processor system that may be used to implement systems and methods described herein.

FIG. 4 is a block diagram of an example processor system 410 that may be used to implement systems and methods described herein. As shown in FIG. 4, the processor system 410 includes a processor 412 that is coupled to an interconnection bus 414. The processor 412 may be any suitable processor, processing unit, or microprocessor, for example. Although not shown in FIG. 4, the system 410 may be a multi-processor system and, thus, may include one or more additional processors that are identical or similar to the processor 412 and that are communicatively coupled to the interconnection bus 414.

The processor 412 of FIG. 4 is coupled to a chipset 418, which includes a memory controller 420 and an input/output ("I/O") controller 422. As is well known, a chipset typically provides I/O and memory management functions as well as a plurality of general purpose and/or special purpose registers, timers, etc. that are accessible or used by one or more processors coupled to the chipset 418. The memory controller 420 performs functions that enable the processor 412 (or processors if there are multiple processors) to access a system memory 424 and a mass storage memory 425.

The system memory 424 may include any desired type of volatile and/or non-volatile memory such as, for example, static random access memory (SRAM), dynamic random access memory (DRAM), flash memory, read-only memory (ROM), etc. The mass storage memory 425 may include any desired type of mass storage device including hard disk drives, optical drives, tape storage devices, etc.

The I/O controller 422 performs functions that enable the processor 412 to communicate with peripheral input/output ("I/O") devices 426 and 428 and a network interface 430 via an I/O bus 432. The I/O devices 426 and 428 may be any desired type of I/O device such as, for example, a keyboard, a video display or monitor, a mouse, etc. The network interface 430 may be, for example, an Ethernet device, an asynchronous transfer mode ("ATM") device, an 802.11 device, a DSL modem, a cable modem, a cellular modem, etc. that enables the processor system 410 to communicate with another processor system.

While the memory controller 420 and the I/O controller 422 are depicted in FIG. 4 as separate blocks within the chipset 418, the functions performed by these blocks may be integrated within a single semiconductor circuit or may be implemented using two or more separate integrated circuits.

According to certain embodiments considered as examples in the present application, media files imported from a medical imaging device into a PACS are optionally subjected to a layered incremental compression. Certain media files are grouped in sequences called series, and certain series are grouped into studies, where each study represents a total set of media associated with a single medical exam. Each such study can be optionally attributed to a study type, where each study type is associated with a certain protocol for study interpretation. The protocol can include but is not limited to an order and positions for series display, configuration of a toolbar, annotation and measuring tools, and/or other data required for more efficient presentation of diagnostic images and rendering of a diagnosis. The set of tools and resources is referred to as a "study layout."

For each study registered in the database, an algorithm (e.g., a unique algorithm) exists for creation of a list of respective series and individual images included in the study and selection of a proper layout for study display. Upon getting a request for study display, the server first generates comprehensive lists of media files to be used for reading the study and a related layout for study display. These lists are transferred to a client workstation and copies are kept on the server. According to the generated list of media files and a chosen layout for their presentation on the client workstation, a plan for transferring and optional processing and/or decompression of the media files is built and coordinated between client and server.

According to that plan, a first batch of media transfer includes a minimum amount of compression layers to deliver a coarse enough representation of the image(s) provided such that the coarse representation, while not suitable for diagnostic reading, is sufficient for navigating between the images to review the whole study and then focus on images with high diagnostic value. Upon presentation of the images on the diagnostic or other workstation, tools are offered to an operator for implementation of a diagnostic workflow or other relevant workflow. For example, tools can include but are not limited to: scrolling through the stack of images, adjusting brightness/contrast of the images, making measurements and annotations of the images, rendering some other representation(s) such as three-dimensional (3D) or oblique slicing, dictation and reporting tools, and/or other relevant tools.

In certain embodiments, an image transferring and decompression plan prioritizes images such that media images that are currently visible on a client workstation have highest priority for transfer and decompression of fine resolution layers. Thus, images that are currently being reviewed to extract diagnostic features are more quickly transferred and decompressed in their fine resolution representation, so that each currently visible image more quickly reaches diagnostic quality, thus reducing perceived waiting time for a diagnostician.

In certain embodiments, an image transferring and decompression plan prioritizes images such that those images that are currently not visible on a workstation display but have a high probability of becoming visible due to some interactive input of the user (e.g., user scrolling of the image stack) also have sufficiently high priority for transfer and decompression of their fine resolution layers. However, this priority may be lower than a priority for visible image layers, for example. According to one implementation of the transfer and decompression plan, those images reach the client workstation in their diagnostic quality soon after visible images thus reducing the latency time experienced by a diagnostician upon scrolling through the image stack or any other scenario of re-focusing from one diagnostic image to the other.

In certain embodiments, an image transferring and decompression plan is sensitive to user interaction upon implementation of a diagnostic reading workflow. For example, upon scrolling of any available image stack, statuses of all images change, making some currently invisible images visible and making some currently visible images invisible. The status changes are communicated to subsystems responsible for image transfer and decompression, triggering changes in implementation of the loading plan by changing priorities of transfer and decompression of individual images in coordination with changing image status.

While certain embodiments are described with respect to utilization of layered compression and related diagnostics, other embodiments are not limited to these approaches in other information systems. Certain embodiments can also apply to information and archiving systems used for storage of uniform data or for different types of data and media. Certain embodiments can apply to information systems wherein one of the targets of the information system is delivery of stored data to an application for interactive handling, subsequently referred to as "reading," and implemented though a reading computer application. Reading can be implemented according to a plurality of different scenarios or workflows further referred as "reading workflows." Each workflow can involve a different nature of the data set available for reading application. The data set can include data of the same type or of multiple types. Different types of data for each workflow can be of different volume and can be used at different stages of the reading workflow.

Since an information system cannot deliver an entire data set for a reading workflow instantly, certain latency or "idle time" is introduced for an operator implementing the reading workflow. Latency can be caused by, for example, limited bandwidth of communication lines, limited speed of data retrieval from storage media, limited speed for data search, and/or other technological or non-technological limitation.

Certain embodiments reduce latency in delivering images for a reading workflow by providing an image loading plan. The plan includes a description of reading workflows implemented and stored. The description can include, for example, a description of data types and data instances for successful running of the reading workflow. The description can also include a technical mechanism used for retrieval and delivery to a reading application of particular data instances for each particular instance of a reading workflow.

The loading plan can also include, for example, a description of what data should be available on a client workstation at any stage of the reading workflow in accordance with its normal implementation or in reaction to interactive actions of the operator. The description can specify data that should be delivered to the workstation for implementation of the next stages of the reading workflow upon most probable interactive interventions of the operator, for example.

Delivery engines and other hardware/software can be arranged in a delivery chain to provide sequential delivery of data or its usable pieces through a chain of information subsystems from original data storage to the client workstation in accordance with the loading plan.

The loading plan and delivery chain can identify that the reading workflow has proceeded to a next step due to a progression of events and/or in response to human interaction. Missing data pieces for a next step of the reading workflow are identified, and missing data information is broadcast to all or selected delivery components. For example, delivery hardware and/or software impacted by the missing data are notified about the missing information.

Loading plans governing sequential actions of delivery components can be reconciled in accordance with proceeding to a next stage of the reading workflow and accounting for the missing data. Reconciliations of the loading plans of different delivery elements are coordinated to help reduce or eliminate data traffic congestions through the delivery chain.

Load on components of the delivery chain(s) that serve several data destinations can be balanced through partitioning between the destinations so that data traffic to all destinations of the same data delivery component is in proportion to a bandwidth of a link between the delivery components and in proportion to a capacity of each data destination to receive and process incoming data and/or data pieces.

In certain embodiments, utilization of lossless, lossy, and/or layered compression can be utilized so that the loading plan(s) can incorporate loading of partial (e.g., lossy) data on certain stages of a reading workflow, with optional increasing of data quality to less lossy or even fully lossless by loading of extra compression layers of the same data.

Thus, certain embodiments provide a PACS configured for importing, storage, access, distribution, and/or interpretation of radiological exams presented as a plurality of digital images and other diagnostic data including but not limited to textual, visual, audio, graphical, and/or other types of data. The PACS can utilize a single data type and/or a combination of different data types with different scenarios for interpretation, management, and/or other functional purposes referred to as workflows, for example. The PACS includes delivery hardware for retrieval of data from physical storage, optional processing of the data, and transferring of the data to a client application. The client application can reside, for example, on the same hardware installation that includes an informational server and physical data storage or on a remote computer connected to the information system through a LAN, WAN, or Internet connection, for example.

The PACS includes one or more delivery engines or dedicated software objects/agents controlling delivery hardware components for delivery of digital data from storage to an end user. Delivery includes but is not limited to retrieval of the data from its original physical storage, optional transmission of the data through a LAN, WAN, Internet, or other connection, and optional compression/decompression or otherwise organized data processing on its way from original physical storage to the end-user client application, for example.

Delivery agents represented by delivery hardware and delivery engines can be optionally arranged in a chain of delivery nodes. Data used by some of delivery nodes for transfer or processing is provided to the delivery nodes by another delivery node called a source delivery node. Data processed or transferred by some other delivery node is used by a subsequent delivery node referred to as a sink delivery node for further transfer and/or processing, for example.

The PACS includes hardware and/or software for creation, storage, and/or modification of data lists including a description of a plurality of data types and a plurality of data objects that should be delivered to a workstation or server for implementation of a workflow. Data lists are retrievable in response to launching a workflow on a workstation or server. Data lists are implemented as explicit lists and/or graphs, recursive lists and/or graphs, on-the fly logical algorithms, and/or other representation, for example.

The PACS establishes one or more loading plans specifying a preferred priority or order for delivery of different objects referred to in a data list to a client/display workstation and/or server in accordance with an implementation of a workflow and/or in accordance with most probable deviations from a workflow implementation resulting from human interactions and/or other factor(s).

The PACS generates a node/engine loading plan for each delivery node/engine based on the general loading plan. The loading plan and/or plans serve as an operational algorithm for the delivery node/engine.

The PACS includes software and/or hardware for reconsideration and reconciliation of a general loading plan and node/engine loading plans for relevant delivery nodes/engines in response to proceeding to a next step of the workflow and/or changing of the workflow implementation, for example.

The PACS can coordinate loading plans for a plurality of delivery nodes/engines along a delivery chain to reduce data congestion along the delivery chain.

The PACS can synchronize reconciliation of node loading plans between delivery nodes serving a workflow.

The PACS includes software and/or hardware for changing a priority, order, and/or speed of data retrieval, transfer, and/or processing by delivery nodes/engines in response to an updated node loading plan.

In certain embodiments, the PACS includes several delivery engines/nodes that concurrently deliver data for several independent workflows. The delivering engine/nodes share common system resource(s) including but not limited to network bandwidth, storage access, CPU, etc. Shared resource(s) impose productivity limitations for concurrent operation of the delivery engines/nodes (referred to as parallel delivery engines/nodes). The PACS also includes hardware and/or software for balancing a load of parallel delivery engines/nodes for fair and effective distribution of shared system resources between several independent workflows.

In certain embodiments, the. PACS includes several delivery engines/nodes arranged in a plurality of delivery chains that concurrently deliver data for a plurality of independent workflows. The delivering engines/nodes share common system resource(s) including but not limited to network bandwidth, storage access, CPU, etc. The shared resource(s) impose productivity limitations for concurrent operation of the delivery engines (called parallel delivery engines/nodes). The PACS includes hardware and/or software that provide load balancing of parallel delivery engines/nodes for distribution of shared system resource(s) between several independent workflows and in consideration of capacity and/or traffic of adjacent source and sink delivery engines/nodes.

In certain embodiments, the PACS stores and/or generates at least selected types of data in compressed form and utilizes loading plan(s) having special provisions for delivery of data compressed to a different degree of lossy compression for initialization of a workflow and/or on different stages of workflow implementation.

In certain embodiments, the PACS includes a general purpose compact or distributed information system designed and used for import, storage, and/or distribution of a uniform data type or data of different natures that includes usage data of a uniform type or a combination of data of different natures within different scenarios (e.g., workflows) of interpretation, management, and/or other functional purpose. The PACS includes delivery hardware from retrieval of data from physical storage, optional processing of the data, and transferring of the data to a client application, provided that the client application can reside either on the same hardware installation that includes an informational server and physical data storage or on remote computer connected to the information system through a LAN, WAN, Internet, and/or other data connection. The PACS includes one or more delivery engines—dedicated software objects/agents controlling delivery hardware component(s) for delivery of digital data from its original storage to an end user. Delivery includes but is not limited to retrieval of the data from its original physical storage, optional transmission of the data through LAN, WAN, Internet, and/or other connection, and optional compression/decompression or otherwise organized data processing as the data is on its way from original physical storage to the end-user application. Delivery agents represented by delivery hardware and delivery engines may be optionally arranged in a chain of delivery nodes such that data used by some delivery node(s) for transfer or processing is provided to the delivery node(s) by another delivery node called a source delivery node, while data processed or transferred by another delivery node is used by a subsequent delivery node called a sink delivery node for further transfer and/or processing. The PACS includes means for creation, storage, and modification of the data lists—a comprehensive description of plurality of data types and plurality of data objects that should be delivered to respective workstation or server for successful implementation of the workflow. The data lists are retrieval in response to launching any workflow on any workstation or server implemented either as explicit lists and/or graphs, recursive lists and/or graphs, on the fly logical algorithms, or other means most proper for any preferred embodiment of the invention. The PACS can establish one or more loading plans representing a preferred priority or order for the delivery of different objects referred to in the data list to respective workstation(s) and/or server(s) in accordance with an implementation of a workflow and/or in accordance with one or more most probable deviations from a normal workflow implementation resulting from human interactions and/or any other factors. The PACS generates a node/engine loading plan for each delivery node/engine based on the general loading plan. The loading plan and/or plans serve as an operational algorithm for a delivery node/engine. The PACS can facilitate reconsideration and reconciliation of the general loading plan and/or node/engine loading plans for all relevant delivery nodes/engines in response to a next step in the workflow and/or changing of the workflow implementation. The PACS can coordinate the loading plans for a plurality of delivery nodes/engines along the delivery chain to reduce data congestion along delivery chain. The PACS can synchronize reconciliation of the node loading plans between all delivery nodes serving a workflow. The PACS can adjust a priority, order, and/or speed of data retrieval, transfer, and/or processing by the delivery nodes/engines in response to an updated node loading plan.

In certain embodiments, the PACS includes several delivery engines/nodes that concurrently deliver data for several independent workflows. The delivery engine/nodes share common system resource(s) including but not limited to network bandwidth, storage access, CPU, etc. The shared resource(s) impose a productivity limitation for concurrent operation of the delivery engines/nodes (referred to as parallel delivery engines/nodes). The PACS can also balance a load of parallel delivery engines/nodes to distribute shared system resources between several independent workflows.

In certain embodiments, the PACS includes several delivery engines/nodes that concurrently deliver data for a plurality of independent workflows arranged in a plurality of delivery chains. The delivery engines/nodes share common system resource(s) including but not limited to network bandwidth, storage access, CPU, etc. The shared resource(s) impose a productivity limitation for concurrent operation of the delivery engines (referred to as parallel delivery engines/nodes). The PACS can also help provide an optimum load balance of parallel delivery engines/nodes to help distribution of shared system resources between several independent workflows and in consideration of capacity and/or traffic of adjacent source and sink delivery engines/nodes, for example.

In certain embodiments, the PACS stores and/or generates at least selected types of data in compressed form and utilizes loading plan(s) having special provisions for delivery of the data compressed to different degree(s) of lossy compression for initialization of a workflow and/or on different stages of workflow implementation.

Using the PACS, image data can be processed, transferred, and displayed in a variety of ways. A few exemplary scenarios are given below for purposes of illustration and are not exclusive.

According to one embodiment, diagnostic images imported by a PACS do not undergo immediate compression if a bandwidth of one or more information links used for delivery of the images to the workstation(s) is wide enough to facilitate prompt downloading of images to the local workstations. The "wide enough" criteria can be established in a plurality of ways including but not limited to: (1) determined by a direct assessment of the actual bandwidth of the data links, (2) set manually upon configuration of the system, (c) a combination of above, etc. According to this embodiment, diagnostic images stored in the system can be further optionally subjected to "aging" compression to reduce a volume of long term storage to either lossless or lossy quality. An exact compression ratio formula can be based on a combination of factors that can be assessed individually for each image or collectively for a plurality of images. Factors include but are not limited to a combination of: diagnostic modality, nature of exam, time elapsed from exam itself and/or from last access to the image(s), institution and/or governmental regulations, etc. The "aging compression" can be optionally scheduled for "low CPU usage hours" and triggered by a combination of factors, the exact formula based on but not limited to combination of: age of the images, time elapsed since last access to images, diagnostic modality and/or nature of the exam, regulations and preferences of institutions, societies and individuals, and/or other factors.

Compression algorithms often attempt to squeeze the volume of the image data as close as possible to a minimum. With multi-slice CT, for example, image data occupies gigabytes because the entry level and images reside on a computer but must be uncompressed, a process which takes time, especially for images processed and compressed by a third party system. Images can be prioritized such that an active image receives priority for loading and the next image behind the active image receives priority as well. If a certain compression method fails to provide sufficient throughput and/or response time, network shortcomings may be addressed instead. For example, a three dimensional viewer may need all volume data decompressed rather than using partial data. Therefore, in certain cases, images may not be compressed at all.

Thus, certain embodiments provide adaptive compression to determine whether to compress or provide image data uncompressed or to provide a combination of compressed and uncompressed image data. In certain embodiments, a PACS server may store two copies, one compressed and one non-compressed, and choose which one to transfer. May choose, for example, if within hospital use non-compressed.

As an example, if a physician is working from home, compression of image data may be appropriate, but the user may not need adaptive compression with prioritization. In certain embodiments, the system can adjust the compression method dynamically as data is being transferred. For example, a transfer may begin with compressed data and then determine that all the images should be transferred for viewing rather a sequence of one by one. However, available processing power may be lower than available bandwidth on the transmission line, so the bottleneck is due to compression. As a result, the remainder of transferred images can be transferred using a decompressed representation. Transmission status can be reviewed again and transmission/compression format can be changed again. Thus, aging compression involves evaluating image data transmission and compression and adjusting compression and/or image resolution based on transmission status, for example.

According to another embodiment, similar to the embodiment described above, images are delivered to a viewing workstation either in a compressed or in an original (non-compressed) format. A decision regarding the delivery format is made by a formula based on a combination of certain factors including but not limited to: a bandwidth of an information link between server and workstation, a type of information link (e.g., local area network (LAN), wide area network (WAN), Internet, virtual private network (VPN), other), processing power of the workstation, institution policy, individual preferences, etc. One or more of the selected factors can be (a) set manually upon configuration of the system and/or setting policy and/or preferences; (b) assessed automatically upon system functioning; (c) by combination of the above; and/or (d) by other suitable method. Selective delivery can be facilitated by keeping multiple copies of the same data in all involved formats or by "on-demand" preparation of a particular format from one or more storage format(s) by a processing engine.

According to another embodiment, images and data used for rendering a first screen on a display workstation and initiating a corresponding interactive or automated workflow are delivered in a special "start up" format. The format is one effective for reducing latency time in awaiting the first visual screen and/or other resources for initiation of the workstation's workflow. The start-up format is defined by a formula based on a combination of certain factors including but not limited to: bandwidth of an information link between server and workstation, a type of link (e.g., LAN, WAN, Internet, VPN, etc.), processing power of the workstation, institution policy, individual preferences, etc. One or more of the selected factor(s) can be (a) set manually upon configuration of the system and/or setting policy and/or preferences; (b) assessed automatically upon system functioning; (c) by a combination of the above; and/or (d) by other suitable method.

The "start-up" data format can be predetermined and securely stored on the server, or created on-demand by conversion from a storage format by a processing engine. Subsequent data delivered to the workstation after initiation start-up screen and workflow can be delivered by other loading format(s) and/or other loading plan(s) including but not limited to those disclosed in other embodiments.

The special start up or initial format can be implemented in a variety of ways. For example, the special format can be an overview screenshot of certain images but not a single individual image. This first content for the screen can be prepared in advance. An image study can be reviewed to create a metadata file describing the whole study but not building the study. Building the study can be performed by retrieving images with the same study number from an image database, for example, and delivered to a client workstation in digested form while the pre-form first content (e.g., a static first view) is being displayed to a reviewing physician at the client workstation. For example, a pre-generated first view typical for that workstation, such as a static overview image, can be provided to allow the physician to spend a few seconds looking rather than being idle and waiting for image delivery.

According to another embodiment, an information system imports a series of images that represent substantially parallel cross-sections of a patient anatomy and sweep some anatomical volume with high density of substantially adjacent image. Thus, the series of images provides high spatial resolution at least in a direction normal to the planes of cross-sections. According to this embodiment, the image series can be subjected to "aging consolidation" by grouping an initial series of images into a plurality of spatially confined and successively adjacent groups of images and consolidating a plurality of consecutive images belonging to a same spatially confined group into one image or another plurality of images with reduced spatial resolution while substantially representing an anatomical slab covered by a respective group of initially non-consolidated of images.

Image slice consolidation can be achieved by a variety of methods including but not limited to: combining respective pixels of neighboring images into one pixel; combining a plurality of neighboring pixels of the same image into one pixel; and/or combining respective groups of neighboring pixels on neighboring slices into one pixel, for example.

As discussed above, combining respective pixels of neighboring images into one pixel can be achieved by a variety of methods including but not limited to: mean value, median value, maximum value, minimum value, etc. Combining a group of neighboring pixels of the same image into one pixel can be achieved by a variety of methods including but not limited to: mean value, median value, maximum value, minimum value, etc. Combining respective groups of neighboring pixels on neighboring slices into one pixel can be achieved by a variety of methods including but not limited to: mean value, median value, maximum value, minimum value, etc.

The method used and consolidation formula are based on the combination of factors including but not limited to: diagnostic modality, initial spatial resolution, nature of exam, time elapsed from exam and/or from last access to the data, institution and/or governmental regulations, etc. Consolidation can be scheduled for "low CPU usage hours" and triggered by a scheduling formula based on a combination of factors including but not limited to: age of the images; time elapsed since last access to images, diagnostic modality and/or nature of the exam, regulations and preferences of institutions, societies and individuals, etc.

CT scanners can produce slices with a thickness of less than 1 mm with high resolution. Rendering three dimensional images involves slices with high resolution. Sometimes high resolution is used when looking for tiny details (e.g., vessels, plaque on vessel walls, etc.) in images. To store these high resolution slices is expensive as is transferring them because a wide bandwidth network is used. Therefore, dedicated workstations are often configured to use high resolution data, which they then send to a PACS workstation as consolidated data (e.g., averaging image data across four slices of 0.7 mm into one slice of 3 mm) so that the PACS workstation displays images of inferior quality to dedicated workstations. However, the PACS can store patient history information and includes diagnostic tools, etc.

Rather than forcing a physician to physically move to a dedicated viewing workstation for better presentation but no additional patient information, which often involves moving from a dark room to a light room and back to a dark room (thus interfering with a physician's vision), certain embodiments provide launching of all such content from a PACS workstation. If a server or other system sends lower resolution data to a PACS workstation and then needs to send high resolution data, two sets of data (e.g., one low resolution and one high resolution) can be sent.

According to another embodiment, the previous embodiment is modified such that in addition to producing a set of consolidated lower resolution images, a difference between initial data and consolidated data is calculated and stored in the system in a form targeted for substantial preserving of high resolution data for its optional usage when diagnostic quality of low resolution consolidated images is not sufficient. Calculating and storing the difference can help improve storage performance and/or reduce storage cost, for example. Storage of the difference between high resolution and low resolution data can include but is not limited to following: the difference is converted to compressed lossless or lossy format and stored together with consolidated data; the difference is converted to another reduced resolution format stored together with consolidated data; the difference is converted to an appropriate format including but not limited to compressed and/or reduced resolution and/or original format, but stored in some storage other than the storage used for consolidated data with lower price per megabyte or for any other practical reason, for example.

Thus, a physician or other user of the system can access aged images with reduced spatial resolution, while having an ability to access the full resolution images in a substantially representative appearance. The substantially representative appearance of the full resolution data can be reconstructed in advance or on-demand by adding to each consolidated image the difference between original image and consolidated one. The difference can be pre-calculated as part of the aging consolidation, for example.

As an example, a reference frame can be stored along with a difference between each reference frame and surrounding intermediate frames. As another example, rather than using every tenth frame as representative image data, an average of each consecutive ten frames is determined to generate a consolidated representation of the anatomical value. Thus, a thick image slice can be created that has image data values as if the slice was generated with an old modality at thickness of, for example, 3 mm rather than 0.7 mm. The thicker slice may be good for comparison but not for sophisticated volume rendered or analysis applications, for example.

For the remainder of the image data, there are many economical ways to store that difference data. For example, a lossy compression can be used to make compromises on low level details but maintain high level difference information between images. Difference data can be maintained on a remote storage with high latency access but low cost, for example. The difference data can have its own life cycle and plan. For example, image difference data may be kept whole on an image archive and, after a year, be subject to lossy compression for further storage. After another year, the compressed data is subject to another lossy compression, and, after five years, the archived difference data is deleted, for example.

Additionally, certain embodiments help to reduce time spent opening a study from a PACS to a local workstation through automatic, configurable pre-loading strategies to automatically pre-load the next study intended for reading to the client workstation and performing data preprocessing before the user starts a diagnostic reading of that study, so that delays associated with study loading are reduced or minimized. Furthermore, certain embodiments provide for negotiation between diagnostic viewer instances invoked at the same time and sharing network bandwidth and processing power on the workstation trying to simultaneously download multiple studies and respond to user interface queries reading the study.

As an example, certain embodiments attempt to maintain a time to display of a first image the same regardless of the study size. The system can identify which images can be delivered first to render an image space for initial review by a radiologist. When images are to be derived from two image series (e.g., a PET CT combined from an image providing metabolic information and an image providing anatomic information), the smaller data set is loaded first. If there are many images, a data set can be concatenated, and loading can start from a reduced data set that is sufficient to be shown to radiologists for studying orientation and navigation between images. While he or she navigates, image downloading continues. A reduced or sparse representation can be created in advance, for example. For example, a volume of data in PET images is much lower than in CT images, but PET images include functional information for a physician to begin his or her analysis. Therefore, some subset that is substantially smaller than the other data can be loaded first. Alternatively or in addition, a subset can be created that is some sampling (e.g., every $3^{rd}$ image, every $5^{th}$ image) of the larger set. Thus, a representative subset of data is created, optionally in a coarser resolution, and also optionally save to the workstation some metadata regarding this reduced subset of images. For example, a series includes one axial image, one lateral image, one image with contrast, one image without contrast. The first series has a certain number of images, and the first image has a certain orientation, for example. If a user wants to open the first image, the application is directed to a certain location in memory. Thus, time is saved not only in transferring the images but also in creating the associated metadata for the images. An application can parse not only the image data but also the metadata for the image.

To provide better performance for mammography integration in particular, certain embodiments provide a new mode of PACS operation referred to herein as AutoFetch. However, use of the name AutoFetch should not be construed to limit embodiments to pre-fetching data from a remote server to a local workstation but is instead used in a broad sense of pre-fetching, pre-arranging, and pre-processing of data according to a preferred scenario of diagnostic reading by a physician. Steps are implemented in the background so that a latency time between finalizing reading of a previous study and starting a next study reading is reduced or minimized, for example.

In certain embodiments, a user is able to turn on and off the AutoFetch functionality which pre-loads one or more studies according the order of the studies on a worklist. A user can specify certain parameters of pre-loading, such as a "stay-ahead factor." AutoFetch can negotiate a loading order between multiple instances of a diagnostic viewer. AutoFetch can automatically launch data pre-processing and/or data grooming engines if involved in a mode of diagnostic reading specified for the study. Switching from reading the current study to the next study preloaded by AutoFetch can be done with one mouse click and reduced delay between closing a study and opening the next study, for example.

An efficient reading sequence workflow involves a user marking a worklist as a "reading sequence." More than one worklist for a user can have such a designation. Opening a study from such a worklist initiates the reading sequence. Only one sequence can be active at a time. Opening a study from another worklist while the reading sequence is active will not initiate another sequence.

When a study from the worklist with an active reading sequence opens, the next study on the worklist, unless it is already locked from viewing by a different user, begins downloading in the background (e.g., transparently to the user). The downloading process is given a lower priority so as not to affect performance of reading of the open study. The next study can also be locked from view at this point. The next study is defined as the first study on the worklist (e.g., according to the worklist filter and sorting order) which is not currently open and not locked from view.

If an open study is part of the reading sequence, an "Exit" button or option in the diagnostic viewer includes a modified icon or other option captioned "Next." When user presses the "Next" button, the following operations are performed independently in parallel. The current study is removed from the display, and finishing operations begin in the background. The study presently stored in a data cache is brought into view. The next study to be loaded into the cache is determined and begins loading. Worklist content and an order of studies can be changed at any time due to operations by a current user or other user. Some studies can be read by other users and thus removed from the worklist. Study or patient information can be changed so the no longer satisfies one or more worklist criteria, or the study can be deleted.

A current user can modify worklist criteria or change a worklist sorting order, for example. However, in certain embodiments, for performance reasons, changes to worklist content and/or order are determined periodically, and the next study to load is determined based at least in part on a snapshot of the worklist content. A snapshot of the worklist content can be acquired for a certain number of studies (e.g., defined in a system configuration). The snapshot of the worklist content can be updated when all studies from the current snapshot have been downloaded, for example. Both the currently open study and the cached study are locked from view, but other studies from the current worklist can be read by other users.

In certain embodiments, the sequence of viewing and loading terminates when the user selects a "Finish" option or no studies are left in the worklist. When user selects "Finish," the current viewer performs done operations and closes without bringing up a next loaded study and without initiating AutoFetch for the next study or user. The reading sequence at this point is terminated. Already pre-fetched studies can be accessed through one or more menu or interface options.

A user can switch worklists to look at a different study. Such a study can be opened regularly with the Done button, for example. A user can explicitly open a different study from the reading sequence worklist. This study is also provided with a "Next" button, and pressing the button behaves in the same way for all currently open studies with "Next" button.

In certain embodiments, a user can work simultaneously with more than one PACS system on the same client (for example, in teleradiology). In such systems, going to the Next study indicates going to the next study that has been pre-loaded from the same system as the current study.

When more than one diagnostic viewer downloads studies, the viewers negotiate loading priorities so that only one study is downloaded from a PACS server at any particular time. Decompression of the images not in focus is performed during idle cycles of the client workstation processor.

The steps of the improved diagnostic reading workflow are given above as an example only and certain embodiments of the present invention cover other possible combinations of these steps, their subset or combination of these and other work-steps.

As a further example, if a user has an AutoFetch privilege, AutoFetch on and off items are added to, for example, a right-click menu on a study list worklist to enable and disable AutoFetch for the worklist. When AutoFetch is turned on the worklist is designated as an AutoFetch worklist. When the worklist is designated as an AutoFetch worklist, an AutoFetch enabled icon or identifier can be displayed in conjunction with the worklist name, for example. When AutoFetch off is selected for a worklist, the designation of the worklist as an AutoFetch worklist is removed. In certain embodiments, AutoFetch can be enabled on any worklist except search results.

When a user selects to open one or more studies on a worklist that is designated as an AutoFetch worklist, if no worklists have active AutoFetch, AutoFetch is activated for the selected worklist and one or more studies are opened as described further below. IF the worklist already has an AutoFetch active, the one or more studies are opened as described below. If another worklist already has AutoFetch active, the selected study is opened without AutoFetch.

When a user opens a study with activation of AutoFetch on a worklist, the study opens in the diagnostic viewer. At substantially the same time, in the background, N (e.g., specified by batch size and/or other preferences) viewers are opened with the first studies from the worklist that are not locked from viewing. AutoFetch is set to active. These viewers are opened with AutoFetch active and are loaded in the background with an index 1 to N based on their order in the worklist. If more than one study is selected for opening from an AutoFetch active worklist, the first selected study is opened in the foreground and the others are opened in the background. If a user has turned off or disabled opening multiple studies as an AutoFetch batch process, an additional N viewers are opened with the studies not locked from viewing.

If a user opens a study when AutoFetch is already active for a worklist, the study is opened in the diagnostic viewer. If more than one study is selected for opening, the first study is opened in the foreground with AutoFetch and the others are opened in the background with AutoFetch.

If a user selects one or more prior exams to be opened, if AutoFetch is active and a viewer is launched in the background, the viewer is informed of a maximum number of priors to be fetched along with the current study to be viewed.

If a user requests an identification of the next study, the PACS server responds with an identification of the next study that is not locked from view by this or another user from the beginning of the worklist with an active AutoFetch. In certain embodiments, STAT studies, if present, are considered equally with other studies on the same worklist, for example. If a user changes a sorting order on the worklist, the change is not reflected in the selection of a next study immediately, but rather with a delay that is determined by the number of studies specified by an AutoFetch snapshot size system configuration. A state of the worklist is updated when all studies from the snapshot have been loaded.

If a user selects to deactivate AutoFetch, the study list accepts communication from the diagnostic viewer indicating that the user decided to stop AutoFetch and performs the same actions as if AutoFetch off had been selected on the worklist menu. If a worklist with an active AutoFetch becomes empty, AutoFetch can automatically deactivate, for example. When AutoFetch is deactivated, an AutoFetch indicator associated with the worklist can be removed.

Fetching studies in a worklist with AutoFetch can be accomplished as follows. Studies can be fetched in the background while another study and/or other information are displayed. When a diagnostic viewer is launched with a background switch or indicator, the viewer is minimized and/or is not displayed on the screen. In a Microsoft Windows® task bar and/or other application indicator, an icon or indicator for the viewer can display a percentage of study download completed, for example. When 100% is reached, the name of the viewer/study can be displayed. The viewer can begin downloading a specified study (and a specified number of priors) after the viewer in focus on the display and other viewers in front of the viewer in the fetching queue have completed downloading. After the study and a necessary number of priors, if applicable, are loaded, the viewer remains in the background until it is brought on-screen. The viewer also signals to other viewers that the next viewer in the queue can begin downloading. If a particular study has less than a maximum number of priors specified, only available priors are loaded. If a study has more than a maximum number of priors, only the maximum number are loaded. Studies being downloaded in the background are locked from view. If there are multiple viewers loading studies, the viewers coordinate among themselves so that only a viewer that has focus downloads until completed, and other viewers download afterwards. A sequence between off-focus or background viewers is such that off-focus viewers download before background viewers, and, among off-focus viewers, the viewers download according to a sequence of their launching.

Studies loaded with AutoFetch can be navigated according to a plurality of interface options. When a diagnostic viewer is launched with AutoFetch, a Next button shall appear alone or in conjunction with Done/Finish button options. Selecting "Next" is this mode closes the study as the Done option would do in a non-AutoFetch mode and bring into focus the next viewer from the viewers in the background that has the lowest queue index. Selecting Next also generates a request for identification of the next study from the server and launches a next instance of the diagnostic viewer with AutoFetch and background loading options selected. The next study and a specified number of priors (if any) will be loaded in the background. Selecting Done rather than Next will close the current study without bringing any background viewers up for display or requesting the next study. Selecting Finish closes the study and indicates to the study list that the AutoFetch for this worklist should be deactivated. Additionally, selection of Finish communicates to other viewers that their Next buttons/options will be reverted back to the regular Done button/option. The Done button with the functionality described above can be placed on a patient folder, for example.

When studies are loaded from more than one distinct server with an active AutoFetch, navigation is performed between studies loaded from the same server. In certain embodiments with large installation and business continuity configurations, studies coming from different nodes are not treated as coming from different servers/systems.

In certain embodiments, a variety of user preferences can be set. For example, an AutoFetch batch size preference specifying a number of studies that are pre-loaded when AutoFetch is activated. If batch size is set to zero (0) studies, no study loading is performed. If batch size is N>0 studies, then after the first study is opened, N next studies from the batch are downloaded into a local cache. N studies are maintained in the local cache. If a batch size is not specified, the size will be treated as zero (a default value).

An AutoFetch priors preference includes a numeric value specifying a number of prior studies to be auto-fetched along with the current study when AutoFetch mode is active. If AutoFetch priors is set to zero studies, then no priors are pre-fetched. If AutoFetch priors is M>0 studies, then a maximum of M latest priors are fetched along with the current study. If AutoFetch priors is not specified, then a default of zero is applied.

An open multiple studies as AutoFetch batch preference is a Boolean value (e.g., represented by a checkbox) that specifies whether opening multiple studies by a user on an AutoFetch worklist is treated as creation of an initial batch. If this preference is set to off, an additional N studies are included in a pre-loading batch when multiple studies are open. If this preference is set to on, the studies selected by the user are considered the pre-loading batch. By default, this preference is set to on.

In certain embodiments, an AutoFetch privilege can also be specified to determine whether a user can control AutoFetch functionality.

In certain embodiments, an AutoFetch snapshot size determines a number of studies that are to be included in a snapshot of the AutoFetch worklist.

In addition to information described above defining the workflow associated with the worklists and handling the data transfer between the server and the local workstation, embodiments can also include additional steps for data handling, grooming, and/or pre-processing by the viewers opened in silent or background mode in anticipation of their activation in the course of diagnostic reading. Operations include but are not limited to data processing (e.g., sharpening/smoothing/edge detection, etc.), multi-planar image reconstruction, computer-aided diagnostics based on digital data processing, image registration and/or fusion, image arrangement, requesting additional images and/or related medical data from various data repositories, etc.

Thus, use of a loading plan in conjunction with pre-loading and/or image slice/compression algorithms can help provide a reduction in latency time to open a new exam study.

In certain embodiments, the loading plan can incorporate special provisions to minimize or reduce the time for showing of the first image in a study by parsing the data and metadata for the image up to some subset of the data/metadata that is sufficient to start the workflow. The loading plan can include auxiliary objects not included in the study that are displayed on a user's screen to reduce latency time (e.g., an overview image, a static image, a coarse quality image, etc.).

Certain embodiments can be applied beyond clinical environments to a variety of information systems that support workflows (e.g., air traffic control, shipping systems to track packages, customers, nodes, transportation, etc.). Certain embodiments provide a system that manages retrieval, transportation, and delivery of components. For every stage of the workflow, a certain subset of the objects are needed. The objects (e.g., pieces of information or plywood or concrete) can be stored in various places. The loading plan and a graph of the objects needed at various stages of the workflow can be provided and used. The graph points to different objects, including nested and/or linked objects, involved in the workflow. One object may not care about a context of the other object, and the loading plan can follow pointers or links from one object to the next.

For example, a diagnostic viewer is directed to retrieve images for a radiologist user. The viewer does not already know what images are involved but can access a descriptive file which indicates the images involved and indicates that a first series is a consolidated series with thick resolution slices with a high resolution difference stored elsewhere, for example. As an example, the viewer only needs the consolidated series for a first displayed series but needs high resolution images for a third displayed series. Objects or images for viewing can be loading using a loading plan for objects and a loading graph including a knowledge of the location(s) of the objects and how the objects can be delivered. The loading plan includes information describing image and information layout for the viewer.

The loading plan for the data is used in conjunction with a plurality of data delivery nodes that are notified that they are to deliver the specified data objects. Each node can have loading plans for various customers and the nodes balance the load according to the various loading plans. As an example, different nodes should know about bottlenecks ahead of them and should not use all resources for one user because that user's computer has a processor with low processing power and, even if all requested images are delivered to that user's computer, the user will still be waiting for the images to be decompressed.

Thus, for display of images via a diagnostic viewer and/or other task involving objects for retrieval and use, there is a graph of objects needed for each step and a loading plan to load those objects. The loading plan is delivered to all nodes needed to carry those objects. Each node/broker is a transportation agent and has a loading plan combined from the loading plans of all of its clients. When each transportation broker multi-threads delivery of various objects to various clients, the broker balances demands of the clients taking into account further nodes and further bottlenecks that can occur down the delivery chain. The work/loading plan can also change. For example, a system is loading images one by one but launching of a third party application involves using all available images at once, so the loading plan is changed to accommodate loading of all images together.

Figure 5:
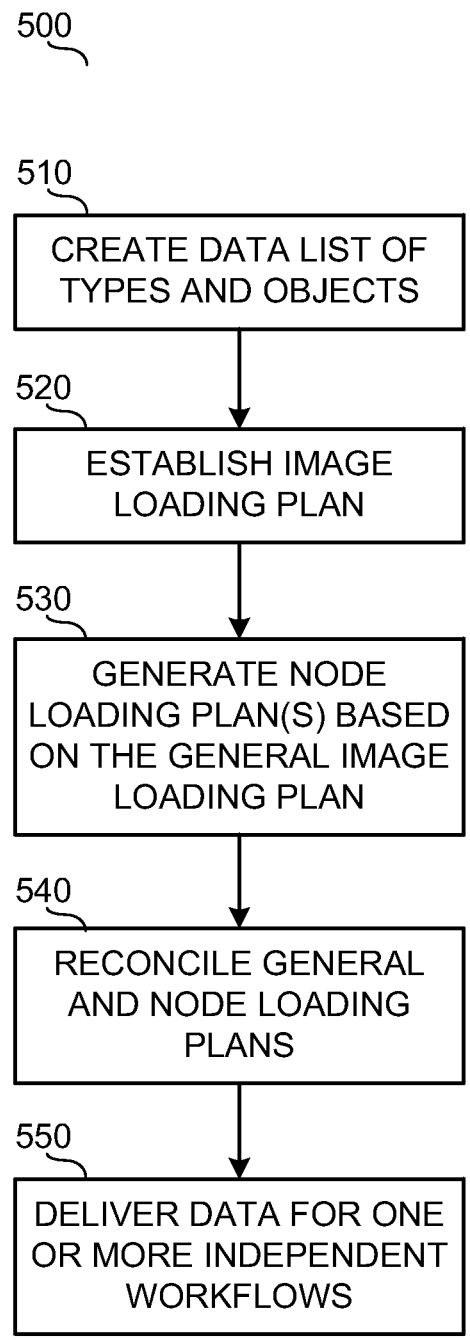
FIG. 5 illustrates a flow diagram for a method for transferring images for display at a client workstation in accordance with an embodiment of the present invention.

FIG. 5 illustrates a flow diagram for a method 500 for transferring images for display at a client workstation in accordance with an embodiment of the present invention. At 510, a data list is created describing data types and data objects to be delivered to implement an imaging workflow. In certain embodiments, the data list can be represented as a graph or other structured representation of resources, for example.

At 520, one or more image loading plans are established to specify a recommended priority or order for delivery of objects referred to in the data list. The loading plan includes a description of image reading workflows including data types and data objects for executing of the reading workflow. The description can also include a technical mechanism for retrieval and delivery of particular data objects to a reading application for a reading workflow. The loading plan can also include, for example, a description of which data should be available to a viewing workstation application at one or more given stages of the reading workflow. Delivery engines/nodes and other hardware/software can be arranged in a delivery chain to provide delivery of data from storage to a viewing workstation in accordance with the loading plan.

At 530, a node or engine loading plan can be generated for each delivery node/engine based on the general loading plan. The node/engine loading plan serves as an operational algorithm for a particular delivery node/engine. The loading plan(s) include one or more priorities for handling of resources involved in image display.

At 540, the general loading plan and/or node/engine loading plans are reconciled. For example, loading plans can be coordinated for a plurality of delivery nodes/engines to reduce data congestion and bottlenecks along the delivery chain. A priority, order, and/or speed of data retrieval, transfer, and/or processing by delivery nodes/engines can be changed in response to an updated node/engine loading plan resulting from multiple loading plan conflict, resource availability, and/or user input, for example. Intermediate engines (e.g., services, data storage, etc.) can be synchronized using loading plan(s) to help avoid bottlenecks, for example.

At 550, data is concurrently delivered by delivery engines/nodes for one or more independent workflows. Data delivery can be facilitated using shared resources according to the loading plan(s). Load balancing of parallel delivery engines/nodes can be performed for distribution of shared system resources between independent workflows. Data can be delivered using one or more compression strategies, data types, etc., in conjunction with the loading plan(s) and data list, for example. A special start up of initial format can be implemented to display some initial information to a user while loading additional image data in the background for replacement on the display. A time for showing of a first image can be reduced by parsing the data for the image and related metadata up to a subset that is sufficient to start the image display workflow.

As an example, the next viewing application can be pre-loaded in the background, and the viewing application can initiate a study opening workflow in the background. When a reviewing physician finishes reading the first study, he or she automatically goes to the next view from background to foreground. The next view is then loaded and ready with tools, hanging protocol, and related prior images (if applicable) configured and ready for view, for example.

One or more of the steps of the method 500 may be implemented alone or in combination in hardware, firmware, and/or as a set of instructions in software, for example. Certain examples may be provided as a set of instructions residing on a computer-readable medium, such as a memory, hard disk, DVD, or CD, for execution on a general purpose computer or other processing device.

Certain examples may omit one or more of these steps and/or perform the steps in a different order than the order listed. For example, some steps may not be performed in certain examples. As a further example, certain steps may be performed in a different temporal order, including simultaneously, than listed above.

Thus, certain embodiments provide for creation and use of one or more loading plans for delivery of image data for viewing. A loading plan can include auxiliary objects not included in an image study that are displayed on a user's screen initially to reduce effective latency time for study display. Loading plans can be applied to a variety of information systems that support workflows (e.g., air traffic control, shipping systems to track packages, customers, nodes, transportation, etc.). Certain embodiments provide systems and methods to manage retrieval, transportation, and delivery of data objects to be combined for display and/or interaction by a user. For each stage of a workflow, a certain subset of the objects is utilized. The objects (e.g., pieces of information or materials) can be stored in various places. For a worklist, the loading plan is used in conjunction with a list or graph of the objects for various stages of the workflow. The graph points to different objects and can be nesting or linked graph/list, for example. One object may not care about the context of another object, and the loading plan can follow pointers in the graph to identify the relevant object(s).

For example, a viewer requests images for display. The viewer does not have a complete picture of the images involved but accesses a descriptive file that indicates the images are series one, two, and three. Image series one is a consolidated series with thick resolution slices and high resolution difference information stored at another location. Only consolidated images are used for series 1 in the display request, but high resolution images are used for series three. A loading plan and loading graph are generated with knowledge of the location of the image series objects and how the objects can be delivered. The loading plan includes the desired image layout for display. The loading plan for the data is relayed to several nodes in the delivery chain to notify the nodes that the nodes are to deliver certain objects. Each node may have loading plans for various customers and balances the load between the plans. Different nodes are informed of bottlenecks ahead of them and adaptively determine resource usage for one or more users based on resource availability and congestion in this and surrounding nodes.

Thus a node serves as a transportation agent or broker with a loading plan combined from loading plans of all of its clients. When each transportation broker multithreads delivery of various objects to various clients, the broker balances demands of the clients taking into account surrounding nodes and bottlenecks in the delivery chain of nodes. Additionally, a loading plan can change. For example, a current request involves loading images one at a time but launching of a third party application on the client workstation involves utilizing all available images at once, so the loading plan is changed to request loading of all images together. Thus, status updates can be passed to nodes to allow those nodes to reconsider and possibly alter their loading plans.

Thus, certain embodiments help improve an efficiency of delivering information to client workstations to reduce latency time and load on a clinical information system, such as a PACS. Users typically request a selected part of available content for initial review. Even if all of a study's content is available, reading may be delayed waiting for additional information and/or metadata, such as hanging protocol information, prior exam information, etc. For each specific study, using a loading plan, information involved in the reading process can be algorithmically identified and retrieved. Some of the information is needed before action can be taken in the reading workflow, while other information is not involved until later in the reading workflow. A list of resources for the exam/study and a priority of handling these resources, as well as how the resources should be loaded onto the reading workstation, are provided to intermediate engines (services, data storage, etc.), which are synchronized according to the plan so that loading, storing, packaging are synchronized and bottlenecks are reduced or avoided. As one example, pre-fetching or pre-loading can be used to assist in loading and prioritizing of images and related data for display.

For example, "smart" prefetching of a next to be read study from a worklist of a client viewing workstation can be performed according to a loading plan. A physician, for example, reads studies in a predefined order coinciding with the worklist ordered according to his/her criteria. When the first study is retrieved from the worklist upon initiation of the reading workflow, a certain number of next studies are anticipated and preloaded on the workstation. Rather than preloading a context and caching the context on the workstation, a next viewing application is loaded in the background. A workflow of opening that next study (including hanging protocols, related prior studies for comparison, etc.) is initiated in the background on the workstation. When the physician finishes reading the first study, rather than going to the worklist and opening the next study, the physician is automatically brought to the next view, which goes from background to foreground. The next view is already loaded with tools, a hanging protocol, and prior images configured and ready for review.

In certain embodiments, no physical location on a client workstation disk or memory contains sensitive patient information. The viewer uses protected memory space available to the viewing application for loading and display. If a power surge or termination of process occurs, no sensitive information is exposed. The protected memory is cleared upon reboot of the computer.

Certain embodiments provide a technical effect of improved diagnostic reading efficiency through reduction of latency time for opening new exams. Images and related data and metadata are pre-loaded into local storage so that data is more immediately available when the user requests review of the next exam. Image(s) are transferred to a local machine so that display and interaction can be faster. A worklist can be configured to allow or prohibit local storage, processing, and/or viewing of images and related information.

It should be understood by any experienced in the art that the inventive elements, inventive paradigms and inventive methods are represented by certain exemplary embodiments only. However, the actual scope of the invention and its inventive elements extends far beyond selected embodiments and should be considered separately in the context of wide arena of the development, engineering, vending, service and support of the wide variety of information and computerized systems with special accent to sophisticated systems of high load and/or high throughput and/or high performance and/or distributed and/or federated and/or multi-specialty nature.

Certain embodiments contemplate methods, systems and computer program products on any machine-readable media to implement functionality described above. Certain embodiments may be implemented using an existing computer processor, or by a special purpose computer processor incorporated for this or another purpose or by a hardwired and/or firmware system, for example.

One or more of the components of the systems and/or steps of the methods described above may be implemented alone or in combination in hardware, firmware, and/or as a set of instructions in software, for example. Certain embodiments may be provided as a set of instructions residing on a computer-readable medium, such as a memory, hard disk, DVD, or CD, for execution on a general purpose computer or other processing device. Certain embodiments of the present invention may omit one or more of the method steps and/or perform the steps in a different order than the order listed. For example, some steps may not be performed in certain embodiments of the present invention. As a further example, certain steps may be performed in a different temporal order, including simultaneously, than listed above.

Certain embodiments include computer-readable media for carrying or having computer-executable instructions or data structures stored thereon. Such computer-readable media may be any available media that may be accessed by a general purpose or special purpose computer or other machine with a processor. By way of example, such computer-readable media may comprise RAM, ROM, PROM, EPROM, EEPROM, Flash, CD-ROM or other optical disk storage, magnetic disk storage or other magnetic storage devices, or any other medium which can be used to carry or store desired program code in the form of computer-executable instructions or data structures and which can be accessed by a general purpose or special purpose computer or other machine with a processor. Combinations of the above are also included within the scope of computer-readable media. Computer-executable instructions comprise, for example, instructions and data which cause a general purpose computer, special purpose computer, or special purpose processing machines to perform a certain function or group of functions.

Generally, computer-executable instructions include routines, programs, objects, components, data structures, etc., that perform particular tasks or implement particular abstract data types. Computer-executable instructions, associated data structures, and program modules represent examples of program code for executing steps of certain methods and systems disclosed herein. The particular sequence of such executable instructions or associated data structures represent examples of corresponding acts for implementing the functions described in such steps.

Embodiments of the present invention may be practiced in a networked environment using logical connections to one or more remote computers having processors. Logical connections may include a local area network (LAN) and a wide area network (WAN) that are presented here by way of example and not limitation. Such networking environments are commonplace in office-wide or enterprise-wide computer networks, intranets and the Internet and may use a wide variety of different communication protocols. Those skilled in the art will appreciate that such network computing environments will typically encompass many types of computer system configurations, including personal computers, hand-held devices, multi-processor systems, microprocessor-based or programmable consumer electronics, network PCs, mini-computers, mainframe computers, and the like. Embodiments of the invention may also be practiced in distributed computing environments where tasks are performed by local and remote processing devices that are linked (either by hardwired links, wireless links, or by a combination of hardwired or wireless links) through a communications network. In a distributed computing environment, program modules may be located in both local and remote memory storage devices.

An exemplary system for implementing the overall system or portions of embodiments of the invention might include a general purpose computing device in the form of a computer, including a processing unit, a system memory, and a system bus that couples various system components including the system memory to the processing unit. The system memory may include read only memory (ROM) and random access memory (RAM). The computer may also include a magnetic hard disk drive for reading from and writing to a magnetic hard disk, a magnetic disk drive for reading from or writing to a removable magnetic disk, and an optical disk drive for reading from or writing to a removable optical disk such as a CD ROM or other optical media. The drives and their associated computer-readable media provide nonvolatile storage of computer-executable instructions, data structures, program modules and other data for the computer.

While the invention has been described with reference to certain embodiments, it will be understood by those skilled in the art that various changes may be made and equivalents may be substituted without departing from the scope of the invention. In addition, many modifications may be made to adapt a particular situation or material to the teachings of the invention without departing from its scope. Therefore, it is intended that the invention not be limited to the particular embodiment disclosed, but that the invention will include all embodiments falling within the scope of the appended claims.

The invention claimed is:

1. A computer-implemented method for transferring image data via a delivery chain for display at a client workstation, said method comprising:
    establishing, using a processor, a general loading plan to specify a recommended priority for delivery of image data in a data list, the data list describing image data to be delivered to implement an imaging workflow, wherein the general loading plan includes a description of 1) an associated imaging workflow, 2) data involved for each stage of the associated imaging workflow and 3) an appropriate retrieval and delivery mechanism for each stage of the imaging workflow;
    generating, using a processor, a node loading plan for each node in the delivery chain, the node loading plan to be separate from but based on the general loading plan and the imaging workflow, wherein the node loading plan for a node is to serve as an operational algorithm for the node;
    reconciling, using a processor, the general loading plan and the node loading plan for each node in the delivery chain; and
    delivering, using a processor, the image data via the nodes of the delivery chain based on the general loading plan, the node loading plan for each node in the delivery chain, and the data list.

2. The method of claim 1, wherein the data list is represented as a graph of resources.

3. The method of claim 1, wherein a node in the delivery chain includes a plurality of node loading plans for a plurality of image data delivery workflows.

4. The method of claim 1, wherein reconciling further comprises coordinating loading plans for a plurality of delivery nodes to reduce data congestion and bottleneck along the delivery chain.

5. The method of claim 1, wherein reconciling further comprises changing at least one of priority, order, data retrieval speed, data transfer speed, and data processing by nodes in the delivery chain in response to an updated node loading plan resulting from at least one of loading plan conflict and resource availability.

6. The method of claim 1, wherein delivering further comprises concurrently delivering image data by nodes in the delivery chain for a plurality of independent workflows.

7. The method of claim 1, further comprising employing a compression strategy with respect to the image data for delivery of the image data in conjunction with the general loading plan, the node loading plan for each node in the delivery chain, and the data list.

8. The method of claim 1, further comprising displaying initial information for a user while delivering the image data in a background of the client workstation processing.

9. The method of claim 1, further comprising pre-loading a next viewing application with next image data in the background while the image data delivered is viewed on the client workstation.

10. The method of claim 9, wherein the pre-loading includes loading the next image data with tools, a hanging protocol, and applicable prior images configured and ready for viewing at the client workstation.

11. A picture archiving and communication system, said system comprising:
    a delivery chain including a of nodes retrieving image data from storage and transmitting the image data from a server to a workstation for display;
    a processor and associated memory including a data list and a general loading plan, the data list describing image data to be delivered to implement an imaging workflow and the general loading plan to specify a recommended priority for delivery of the image data in the data list, the processor providing a node loading plan to each node in the delivery chain, the node loading plan to be separate from but based on the general loading plan and the imaging workflow, wherein the node loading plan for a node is to serve as an operational algorithm for the node, wherein the general loading plan and the node loading plan for each node in the delivery chain are to be reconciled in according with the imaging workflow, and
    wherein the general loading plan includes a description of 1) an associated imaging workflow, 2) data involved for each stage of the associated imaging workflow and 3) an appropriate retrieval and delivery mechanism for each stage of the imaging workflow, and
    wherein the delivery chain operates with the data list, general loading plan, and each node loading plan to deliver requested image data via the delivery chain.

12. The system of claim 11, wherein the data list is represented as a graph of resources.

13. The system of claim 11, wherein a node in the delivery chain includes a plurality of node loading plans for a plurality of image data delivery workflows.

14. The system of claim 11, wherein the processor and the delivery chain coordinate node loading plans for a plurality of delivery nodes to reduce data congestion and bottleneck along the delivery chain.

15. The system of claim 11, wherein the processor adjusts at least one of priority, order, data retrieval speed, data transfer speed, and data processing by nodes in the delivery chain in response to an updated node loading plan resulting from at least one of loading plan conflict and resource availability.

16. The system of claim 11, wherein nodes in the delivery chain concurrently deliver for a plurality of independent workflows based on a plurality of node loading plans.

17. The system of claim 11, wherein the processor and the delivery chain employ a compression strategy with respect to the image data for delivery of the image data in conjunction with the general loading plan, the node loading plan for each node in the delivery chain, and the data list.

18. The system of claim 11, further comprising displaying initial information for a user while delivering the image data in background processing of the workstation.

19. The system of claim 11, wherein the processor pre-loads a next viewing application with next image data in the background at the workstation while the image data delivered is viewed on the workstation.

20. The system of claim 19, wherein the pre-loading includes loading the next image data with tools, a hanging protocol, and applicable prior images configured and ready for viewing at the workstation.

21. The system of claim 11, wherein the processor resides on at least one of a picture archiving and communications server and the workstation, and wherein the delivery chain resides on the picture archiving and communications server and a network connecting the server with the workstation.

22. A tangible computer readable medium having a set of instructions for execution on a computing device, the set of instructions executing a method for transferring image data via a delivery chain for display at a client workstation, the method comprising:
  establishing a general loading plan to specify a recommended priority for delivery of image data in a data list, the data list describing image data to be delivered to implement an imaging workflow, wherein the general loading plan includes a description of 1) an associated imaging workflow, 2) data involved for each stage of the associated imaging workflow and 3) an appropriate retrieval and delivery mechanism for each stage of the imaging workflow;
  generating a node loading plan for each node in the delivery chain, the node loading plan to be separate from but based on the general loading plan and the imaging workflow, wherein the node loading plan for a node is to serve as an operational algorithm for the node;
  reconciling the general loading plan and the node loading plan for each node in the delivery chain; and
  delivering the image data via the nodes of the delivery chain based on the general loading plan, the node loading plan for each node in the delivery chain, and the data list.

* * * * *